(12) United States Patent
Petty et al.

(10) Patent No.: US 6,478,961 B2
(45) Date of Patent: Nov. 12, 2002

(54) DEVICE FOR SEQUESTRATION AND CONCENTRATION OF POLAR ORGANIC CHEMICALS FROM WATER

(75) Inventors: Jimmie D. Petty, Columbia, MO (US); James N. Huckins, Columbia, MO (US); David A. Alvarez, Columbia, MO (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 0 days.

(21) Appl. No.: 09/881,244

(22) Filed: Jun. 15, 2001

(65) Prior Publication Data

US 2002/0036166 A1 Mar. 28, 2002

Related U.S. Application Data

(60) Provisional application No. 60/234,949, filed on Sep. 26, 2000.

(51) Int. Cl.[7] .......................... B01D 24/00; B01D 63/00
(52) U.S. Cl. .............................. 210/502.1; 210/500.23; 210/321.8; 210/263

(58) Field of Search .................... 210/651, 500.23, 210/663, 660, 670, 321.8, 321.74, 502.1, 263; 435/2, 31, 32

(56) References Cited

U.S. PATENT DOCUMENTS

| | | | | |
|---|---|---|---|---|
| 5,021,406 A | * | 6/1991 | Maeda et al. |
| 5,139,668 A | * | 8/1992 | Pan et al. |
| 5,916,531 A | * | 6/1999 | Pan |
| 5,972,411 A | * | 10/1999 | Goldstein et al. |
| 6,022,478 A | * | 2/2000 | Baurmeister et al. |
| 6,348,309 B1 | * | 2/2002 | Mohr et al. |

* cited by examiner

Primary Examiner—Ana Fortuna
(74) Attorney, Agent, or Firm—Ross F. Hunt, Jr.

(57) ABSTRACT

A device is provided for the sequestration and concentration of polar chemicals from water. The device includes a microporous hydrophilic membrane enclosure formed by a tube or facing membranes. A mixed sequestration media, contained within the enclosure, transforms dissolved polar organic chemicals into non-mobile species. The sequestration media is a triphasic admixture of a hyper-crosslinked polystyrene-divinylbenzene resin, and a carbonaceous sorbent dispersed on a size exclusion styrene-divinylbenzene copolymer.

19 Claims, 1 Drawing Sheet

DEVICE FOR SEQUESTRATION AND CONCENTRATION OF POLAR ORGANIC CHEMICALS FROM WATER

PRIORITY CLAIM

The present application claims the priority of U.S. Provisional Application No. 60/234,949 filed Sep. 26, 2000.

FIELD OF THE INVENTION

The present invention relates to devices for sampling and sequestration of polar organic chemicals from water so as to permit analysis thereof.

BACKGROUND OF THE INVENTION

Global emissions of persistent bioconcentratable organic chemicals have resulted in a broad variety of adverse ecological effects and human suffering. Consequently, industry has developed less persistent, more water soluble chemicals. However, evidence is growing that the great quantities of these seemingly more environmentally friendly compounds (e.g., herbicides, new generation pesticides, and pharmaceutically related chemicals which have been historically viewed as totally benign) entering aquatic systems on a world-wide basis may be responsible for not only acutely toxic effects, but also are instrumental in causing sub-lethal chronic abnormalities. Adverse effects include altered behavior, neurotoxicity, and severely impaired reproduction. More insidious are the endocrine disrupting effects of exposure to the complex mixture of chemicals present in the environment. Numerous examples, such as increased vitellogenin levels (an estrogen controlled egg protein normally only found in females) in male fish from Las Vegas Wash near Lake Mead, Nev., nonfunctional testes in male alligators in Lake Apopka, Fla., reduced penis size in juvenile male otters in the Columbia River, feminized behavior in male western gulls in southern California, non-descended testicles in male Florida panthers, and masculinized female mosquito fish, unequivocally link such abnormalities to chemical exposures.

Although there are numerous reports on the negative effects of more polar endocrine disrupting chemicals on many forms of wildlife, a heated debate continues regarding the detrimental effects of these chemicals on human health. However, given the danger inherent in wildlife exposure to more water-soluble endocrine disrupting chemicals, and the potential deleterious effects resulting from prolonged human exposure, it is imperative that aquatic systems be monitored for the presence of a wide variety of polar organic chemicals currently entering the environment. While many techniques and methods are available to detect and quantify the non-polar organic contaminants, e.g., the DDT complex, polychlorinated biphenyls (PCBs), etc., of historic concern, similar approaches for waterborne polar organic contaminants are unavailable to environmental scientists. Monitoring of polar organic chemical species, potentially impacting wildlife and humans, and remediation of such contamination will be critical activities for the foreseeable future.

Although there has been considerable effort directed towards development of methods for actively sampling polar organic chemicals from water, this research has centered on the use of solid phase extraction employing specially modified polymeric resins in either a cartridge or imbedded in an inert membrane disk. See Hennion, M. C.; Pichon, V. 1994. Solid-Phase Extraction of Polar Organic Pollutants from Water. *Environ. Sci. Technol.,* 28, 567A–583A; Barcelo/, D.; Hennion, M. C. 1997. Sampling of Polar Pesticides from Water Matrices. *Anal. Chim. Acta,* 338, 3–18; International Sorbent Technology. ISOLUTE Env+® *The new generation of polystyrene polymer SPE columns.* International Sorbent Technology, United Kingdom. Pihlström, T. Hellström, A.; Axelsson, V. 1997. Gas Chromatographic Analysis of Pesticides in Water with Off-line Solid Phase Extraction. *Anal. Chim. Acta,* 356,155–163. Hagen, D. F.; Markell, C. F.; Schmitt, G. A.; Blevins, D. D. 1990. Membrane Approach to Solid Phase Extractions. *Anal. Chim. Acta,* 236, 157–164. Hagen, D. F.; St. Mayr, S. J.; Errede, L. A.; Carr, P. W. 1989. Composite Chromatographic Article, U.S. Pat. No. 4,810, 381, Mar. 7, 1989. Dumont, P. J.; Fritz, J. S. 1995. Effects of Resin Sulfonation on the Retention of Polar Organic Compounds in Solid Phase Extraction. *J. Chromatogr. A,* 691, 123–131; and Slobodnik, J.; Oztezkizam, O.; Lingeman, H.; Brinkman, U. A. th. 1996. The Solid Phase Extraction of Polar Pesticides from Environmental Water Samples on Graphitized Carbon and Empore-Activated Carbon Disk and On-line Coupling to Octadecyl-bonded Silica Analytical Columns. *J. Chromatogr. A,* 750, 227–238.

Laboratories conducting analytical and toxicological research concerning the presence and toxicity of polar organic chemical species critically need sampling and analytical methods capable of defining the presence and amounts of bioavailable polar organic chemical residues.

Unfortunately, current sampling methods are not integrative over sufficient time intervals to sequester adequate amounts of polar organic chemical residues (many of which may have toxicological significance even at ultra-trace levels) to detect trace to ultra-trace levels and to cost effectively detect episodic releases. Also, current sequestration methods are not adequate for integratively isolating sufficient amounts of the mixtures of potentially toxic polar organic chemicals present in aquatic systems for use with bioassay procedures for toxicity testing. It is apparent that no current sampling approach provides a truly integrative method for determining bioavailable polar organic chemical residues. Because no practical sampling method exists that enabled the determination of polar organic chemical species in a passive, integrative manner (existing methods are designed only for point in time monitoring and lack the sensitivity required) at trace to ultra-trace levels, there is a need for a passive, efficient, integrative, and high capacity sampler for polar organic chemical residues.

SUMMARY OF THE INVENTION

The present invention represents a new approach for dealing with major problems associated with toxic polar organic chemicals in the environment, which are of concern to the world at large as well to U.S. governmental agencies such as USGS, FWS, EPA, DOE, NIOSH, OSHA, DOD, etc. This invention can be calibrated for use as a monitoring tool for polar organic chemical residues dissolved in a wide variety of aquatic ecosystems. In addition, other embodiments of this invention can be provided which would apply to large-scale projects such as monitoring industrial emissions, and remediation of point source contamination and the associated release of toxic chemical residues into aquatic ecosystems.

Because the device of the invention can be configured for in situ passive integrative concentration of readily biologically available dissolved phase polar organic chemicals, the invention offers a widely applicable abiotic assessment of organism exposure, thereby overcoming a major shortcoming of current techniques used by government agencies.

Although the invention has other applications, the principal utility of the invention is in monitoring of the time-weighted average potential for exposure of humans and other living organisms to water borne polar organic chemical species. The invention is a very valuable tool for defining the source, transport, and fate/degradation of toxic polar organic chemical residues. Further, because of the integrative sampling construction of the device of the invention, the device is applicable to the reduction of polar organic chemical species in aquatic systems of limited areal extent. This invention is useful to resource managers, regulators, and scientists responsible for determining the impact of chemicals on fish and wildlife resources and human health. The device of the invention enables the measurement of the amounts of polar organic chemical residues present in a broad array of aquatic systems, prediction of their potential adverse effects, and in some cases potential remediation of unacceptably high levels of these chemicals. In brief, government agencies, private sector personnel and members of the scientific community involved in monitoring/regulating environmental contaminants, specifically polar organic chemical species, will have extensive application for this invention.

Before considering the device of the invention in more detail, reference will be made to some background considerations on which the invention is based. Polar organic chemicals enter the environment in a variety of forms ranging from ionic to neutral. Further, many organic chemicals undergo a wide array of biogeochemical-based transformations in the environment, and toxic polar organic chemicals generally impact organisms as dissolved, bio-available species. Moreover, extensive experience with the dialysis of neutral molecules using nonporous polymeric films, the factors controlling sorption of chemicals by a broad array of solid media, and the reaction chemistry of organic chemicals has suggested that development of a passive integrative sampler for polar organic chemical species based on diffusion-controlled uptake of dissolved waterborne-polar organic chemical species and sequestration as non-mobile forms would be feasible.

In general, the device of the invention comprises a sealed microporous hydrophilic polymeric membrane enclosure containing a mixed sequestration phase capable of transforming the dissolved polar organic chemicals into non-mobile (sorbed) species, which accumulate in the device throughout the exposure time. The polymeric membrane is made of thin-walled microporous polymer such as polyethersulfone, nylon, hydrophilic polypropylene, acrylic copolymers, etc. In one embodiment, a thin layer of an appropriate polymer is grafted or laminated to a thicker microporous polymer, such as microporous polyethersulfone, to increase strength and to increase support of the sequestration media. Microporous membranes used in accordance with a preferred embodiment of the invention are characterized by air-filled fixed pores, with the air in the fixed pores being rapidly exchanged with water during the initial contact with water. In one preferred embodiment, the membrane is made of polyethersulfone, and the pores in the polyethersulfone membrane are 0.1 $\mu$m in diameter. The polyethersulfone is hydrophobic as the bulk polymer, but becomes inherently hydrophilic as the polymerized membrane. Polyethersulfone is resistant to most organic solvents with the exception of chlorinated hydrocarbons and is stable in prolonged ($\geq$50 days) contact with water.

In accordance with a preferred embodiment, the sequestration phase comprises a triphasic admixture of a hyper-crosslinked polystyrene-divinylbenzene resin and a carbonaceous sorbent dispersed on a size exclusion styrene divinylbenzene copolymer. In advantageous implementation, the sorbent resin comprises Isolute ENV+ ®, a third generation hyper-crosslinked polystyrene-divinylbenzene resin which has been optimized for the retention of very polar water-soluble organic chemicals. Modifications performed by the manufacturer of this sorbent have resulted in an inherent hydrophilicity, which allows wetting of the resin to occur without the use of organic solvents as intermediaries. Chemical sorption on the resin occurs by electron-donor interactions between the aromatic rings of the resin matrix and the aromatic or $\pi$ bonds of the analyte. The irregularly shaped resin particles have a surface area of 980 m$^2$/g, an average particle size of 80 $\mu$m, and an average pore size of 100 Å. These attributes allow for high recoveries of a wide range of polar organic chemicals. This resin is also stable at any pH, unlike nearly all currently used solid phase sampling devices (i.e., silica-based resins).

The use of carbonaceous sorbents to concentrate organic chemicals has been employed in a wide variety of applications. However, recovery of the chemicals of interest from carbonaceous sorbents is often problematic due to the extreme affinity of activated carbons for organic chemicals. Another commercially available sorbent type, Ambersorbs™, have proven effective in sequestering a variety of organic chemicals. Of these, the Ambersorb 1500 is the most hydrophilic and as with the Isolute ENV+®, this sorbent readily wets without the use of organic solvents. However, as with nearly all carbonaceous sorbents, quantitative recovery of sequestered organic chemicals is problematic. To overcome the recovery problem associated with carbonaceous sorbents in accordance with a further aspect of the invention, a dispersion of Ambersorb 1500™ on a polymeric size exclusion gel was prepared by an adaptation of the procedure described in U.S. Pat. No. 4,303,529, to Huckins, et al (see also Bouvier, E. S. P.; Iraneta, P. C.; Neue, U. D.; Mcdonald, P. D.; Phillips, D. J.; Capparella, M.; Cheng, Y. F. 1998. Polymeric Reversed-Phase SPE Sorbents-Characterization of a Hydrophilic-Lipophilic Balanced SPE Sorbent. *Curr. Trends Sample prep. LC-GC*, May, 1998, S53–S58.) In a specific preferred embodiment, the size exclusion gel comprises Bio Beads SX-3 (commercially available from BioRad, Inc, Hercules, Calif.). This polymeric gel is made from styrene-divinylbenzene copolymer with a 3% cross-linking of the polymer matrix. This degree of cross-linking results in the strongest adherence of carbon particles to the polymer gel. The binding of carbon particles to the polymer matrix is the result of electrostatic and covalent aromatic interactions between the two materials as well as partial inclusion of the carbon particles into the swelled gel pore structure during preparation of the carbon/polymeric gel sorbent. Optimal particle sizes for the carbon range from 0.1 to 50 $\mu$m. Using the procedure previously described the average loading of Ambersorb onto the SX-3 gel was 5%. Other powdered carbons of the requisite size range may be similarly coated onto the SX-3 or similar polymer gels. The use of the limited amount of carbon as a sorbent expands the applicability of the sequestration media for concentrating polar organic chemicals from water, while simultaneously optimizing recovery of the polar organic chemicals from the sequestration media.

Other features and advantages of the invention will be set forth in, or will be apparent from, the detailed description of the preferred embodiments which follows.

DESCRIPTION OF THE PREFERRED EMBODIMENTS

Figure 2:
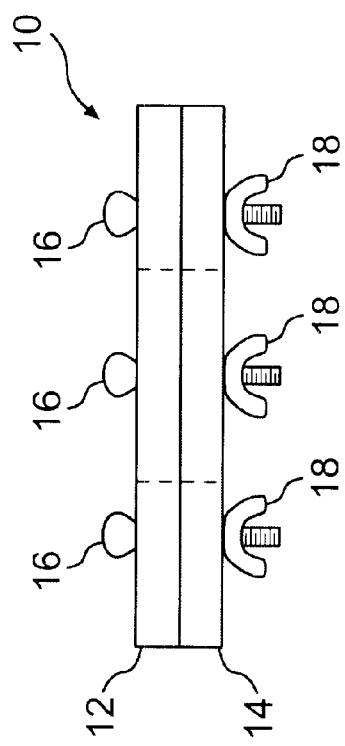
FIGS. 1 and 2 are a top plan view and a side elevational view, respectively, of a sampling device constructed in accordance with one preferred embodiment of the invention.

As indicated above, novel sequestration medium described previously is a triphasic system, which is applicable for the sequestration of a wider range of waterborne polar organic chemicals than any current system. Unlike all current solid phase sorbents, the sequestration medium of the invention is a unique, intimate mixture of sorbents resulting in a system more widely applicable to sequestering waterborne polar organic chemicals than any current system.

The major driving force for uptake of dissolved polar organic chemicals from water, when the device (a mixture of the described sequestrating agents enclosed by a microporous polymeric membrane) is deployed in aquatic systems, is a steep concentration gradient to the sorbent and a low chemical potential once the chemical is sequestered. The maximum rate of sampling is controlled by diffusion of the polar organic chemicals from the ambient water through the pores of the membrane (these water-filled pores are a static barrier to diffusion through the pores of the membrane to the surface of the sorbent admixture). Sorption of the dissolved polar organic chemical by the sequestration phase results in the formation of non-mobile forms of the polar organic chemicals in a water insoluble organic matrix. The transformation effectively removes polar organic chemical species (infinite sink) from one medium and concentrates the sequestered form in a second, isolated medium.

Because of the process described above, the aforementioned polar organic chemical species are concentrated in a linear manner through time. For example, in laboratory experiments it was determined that the uptake rates of three model polar organic chemicals, viz., diazinon, atrazine, and 17α-ethynlestradiol remained constant during a twenty eight (28) day exposure. Mean 28-day sampling rates (expressed as liters/day [L/d] of water cleared of chemical) of the model compounds for a single sampling device with a membrane surface area of about 20 cm$^2$ (contained 100 mg of the sequestration media as an intimate admixture of 2/80 [w/w] SX-3 dispersed Ambersorb 1500/Isolute ENV+) ranged from 0.050 to 0.070 L/d under quiescent conditions to 0.186 to 0.302 L/d for more turbulent systems. The sampling device was found to act as an infinite sink for polar organic chemicals thereby sampling integratively (i.e., providing linear uptake) for prolonged exposures (≧28 days). Also, if devices of sufficient size or numbers are exposed to closed or low exchange rate environments, the polar organic chemical removal rate should be great enough to lower the overall concentrations of waterborne polar organic chemical species. Longer exposure times will result in higher concentration factors above ambient levels.

In some cases the water filled pores of the membrane will control the transport of the waterborne polar organic chemicals to the sequestration medium, i.e., diffusion through the water filled pores. However, if the aqueous diffusional layer on the surface of the hydrophilic membrane is sufficiently large (e.g., under more quiescent conditions), the rate controlling step in the uptake of chemicals by the sequestration media may be diffusion through this boundary layer and not through the water filled pores of the membrane. The total resistance to mass transfer or uptake of polar organic chemicals is the sum of all barriers. The overall resistance ($R_o$) to chemical transfer is defined by the reciprocal of the overall mass transfer coefficient ($k_o$).

$$R_o = l/k_o = I_W/D_W + I_B/D_B K_{BW} + I_M/D_M K_{MW}$$

Where I is the layer or barrier thickness or in the case of $1/k_o$, D is the diffusivity in a given region, K is the partition coefficient, and the subscripts W, B, and M represent the major barriers to mass transfer, specifically the aqueous diffusion layer, the membrane water filled pores, a biofilm layer (surficial growth during deployment of samplers in aquatic systems), and the membrane. Since a significant biofilm layer does not exist under laboratory conditions and indeed does not appear to be produced under field conditions, $I_B=0$ and the overall equation reduces to $$R_o = l/k_o = I_W/D_W + I_M/D_M K_{MW}$$

This equation can be employed to determine the mass-transfer step of greatest resistance (i.e., the rate-limiting step) to polar organic chemical uptake is through the water (i.e., the water filled membrane pores and the aqueous diffusional barrier) or through the polymeric membrane matrix. The diffusion coefficient in the water ($D_w$) can be calculated by the Hayduk and Laudie method (Lyman, W. J.: Reehl, W. F.; Rosenblatt, D. H. *Handbook of Chemical Property Estimation Methods; Environmental Behavior of Organic Compounds*; McGraw-Hill, New York, N.Y., 1982). The diffusion coefficient in a solid (membrane) is 10$^3$ to 10$^4$ times slower than diffusion in a liquid (water). The thickness of the membrane is 152 μm. The membrane pore length, although torturous, is assumed to be approximately the same as the thickness of the membrane. The membrane-water partition coefficient ($K_{MW}$) was experimentally determined under controlled laboratory conditions. Using the aforementioned Hayduk and Laudie method, the $D_w$ values were calculated for the model compounds studied; 4.25×10$^{-6}$, 4.47×10$^{-6}$, 5.25×10$^{-6}$ cm$^2$/s for ethynylestradiol, diazinon, and atrazine, respectively. Using these values and $D_{MS}$ of 10$^{-3}$ to 10$^{-5}$ less than the Dw, it is easily determined that for each model compound studied, the phase with the greatest resistance to mass transfer, and consequently the rate-limiting step for polar organic chemical uptake, is the aqueous diffusional layer and the water filled pores in the membrane. Consequently, under some deployment scenarios, the uptake rate of polar organic chemicals will be controlled by the static conditions present in the approximate 150 μm water filled pores in the membrane.

For the analytical determination of sequestered polar organic chemical residues, recovery and analysis of the polar organic chemical species is accomplished using widely recognized standard techniques (i.e., solvent elution, chromatographic fractionation, high performance liquid chromatography, gas chromatography, gas chromatography/mass spectrometry, liquid chromatography/mass spectrometry, etc.). Any enrichment procedure or analytical technique applicable to measuring polar organic chemical species is suitable for determining concentrations of waterborne polar organic chemicals sequestered by the invention.

Figure 1:
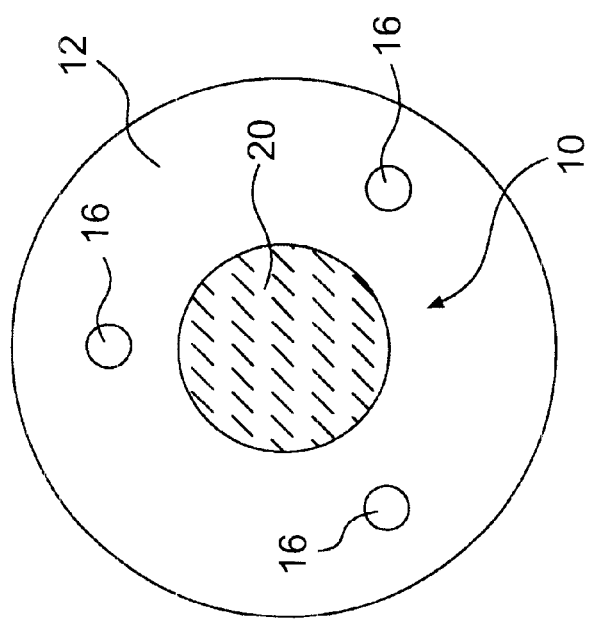

Although the physical configuration of the device of the invention will vary depending on the specific application and its scale, one exemplary embodiment of the invention defined for use in sequestering polar organic chemical species from water is shown in FIG. 1. The embodiment of FIG. 1 was designed for integrative sampling of polar organic chemicals in a laboratory setting and is relatively small in scale. The device, which is generally denoted 10, comprises two stainless steel washers 12 and is equipped with threaded studs 16 and wing nuts 18 as a clamping mechanism. The studs 16 and nuts 18 clamp washers 12 and 14 together for sealing the perimeter of two membranes, one of which, denoted 20, is shown in FIG. 1. In the specific example under consideration, the membranes 20 are 47 mm diameter polyethersulfone membranes, and contain an intimate admixture of Isolute ENV+ and Ambersorb 1500 coated onto SX-3 size exclusion resin. The stainless steel washers 12 and 14 serve to maintain the integrity of the seal enclosing the sampling media.

It will be appreciated that there is a range of possible configurations and process parameters for sequestration of polar organic chemical species from water, including small scale (analytical) devices to larger industrial or remedial scale devices. As indicated above, variety of types of microporous synthetic polymeric films can theoretically be used for the device. These include: cellulose dialysis membrane, hydrophilic polypropylene, nylon, polyethersulfone, other hydrophilic polymeric membranes, and copolymers laminates of microporous polymers. The data presented herein were generated using polyethersulfone. However, each of the above polymers, and others as well, may be effective. Relatively thin polymeric films of 0.001 to 0.0196 inches (2 to 500 $\mu$m) thickness are generally better suited for all applications because of the need to maximize transport of polar organic chemicals through the pores in the polymeric membrane. However, for greater strength, for industrial or large-scale applications, the device should be constructed of thick polymeric membranes to safely hold larger amounts of the sequestration media.

Saturation (generally not approached during ambient water sampling) of the sequestration medium completes the uptake process and requires replacement by another device (s) if monitoring or cleanup is continued. In general, increasing the film thickness of the microporous polymers in order to increase the strength of the device reduces permeation or sequestration rates (typically in a linear manner at constant temperature and pressure) of polar organic chemicals through microporous synthetic polymers. A film thickness of $\leq 160$ $\mu$m is recommended for small scale analytical applications of this invention. However, applications such as those involving the use of large quantities of sequestering agents enclosed in high surface area polymeric films for removal of dissolved polar organic chemicals from various situations may require the greater strength and durability of the upper range of film thickness, i.e., 160 to 500 $\mu$m.

The surface area (polymeric membrane) to mass (enclosed sequestrating medium) ratios used in the device of the invention can vary greatly depending on the nature of the particular application of the device. The larger surface area configurations permit greater total transport per unit time of waterborne polar organic chemicals to the surface of the polymeric sequestration admixture, which increases polar organic chemical removal. Such configurations are typically employed in analytical applications. For some large scale or remedial applications, adequate rates of removal of dissolved polar organic chemicals may require large numbers or long lengths of tubing (exact design requirements must be determined in pilot studies) containing large amounts of the sequestering agents.

An example of a large scale configuration is as follows: approximately 2000 g of an admixture of the sequestering medium (in this example, Isolute ENV+ and Ambersorb 1500 dispersed on SX-3 size exclusion gel) is placed in a three meter length of 15 centimeter wide microporous polyethersulfone tubing having a wall thickness of 0.01 to 0.03 centimeters. The ends of the hydrophilic polymer are sealed, secured with large clamps or the like, and placed in the water of interest. The device so configured can be deployed in multiple single large-scale configuration arrays or in cluster arrays. By employing many of these sequestration phase containing systems, contaminated water can be exposed to large amounts of the sequestration medium for adequate removal of polar organic chemicals.

The sequestration phase can consist of mixtures of two or more sorbents. Examples of such sequestering components are, reverse phase sorbents such as $C_8$, $C_{18}$, etc., styrene-divinyl benzene and other co-polymers, any carbonaceous sorbent applicable to sequestering waterborne organic chemicals, etc. In general, any sequestration medium that will sorb and retain polar organic chemicals can be employed as the sequestration phase in the invention.

Alternate configuration of the invention include the provision of small or large diameter polymeric tubing, or partly sealed polymeric film sheets which provide a very large surface area, which can be arranged in bundles or arrays, etc., secured by means of a frame or other deployment arrangement, filled with the appropriate sequestration phase, and subsequently sealed. Then, these configurations can be placed in contaminated water systems where the water moves or is forced by the arrays and makes intimate contact with the device so as to provide a sampling regimen for removing and concentrating polar organic chemical species. Such an arrangement can be employed for analytical or on an industrial or remediation scale.

Advantages of the present invention over existing approaches for sequestering polar organic chemical species include greater simplicity, reliability (i.e., the device is not prone to mechanical problems or breakdowns), enhanced analytical precision for measurements of bioavailable polar organic chemical residues, improved detection limits for potentially toxic polar organic chemical residues, wider applicability especially in remote unattended situations, and great cost savings. In addition, the invention samples a relatively large window of time, thus providing an estimate of organism exposure. As a result, the invention provides the best estimate of the presence and potential biological significance of exposure to toxic polar organic chemicals in a time weighted integrative manner.

As shown above, the device of the invention was demonstrated to be highly efficient and effective for removing and concentrating several different types of polar organic chemical residues for up to 28 days. Generally speaking, passive sampling of very hydrophilic organic compounds has not been considered feasible or reliable, and no other approach has been demonstrated to be effective. The present invention is unique in that it utilizes a triphasic sampling medium with greatly enhanced sampling characteristics resulting in much higher sampling rates and wider applicability for sampling polar organic chemicals than any current system. The system of the invention sequesters and transforms waterborne polar organic chemicals into a non-mobile form in a passive, time integrated manner. Consequently, the system samples waterborne chemicals over biologically relevant exposure periods and provides a means of addressing the consequences of organism exposure to complex mixtures of polar organic contaminants. The polar organic chemicals can be easily recovered using standard sample processing techniques, with the extract being analyzed by the most widely employed analytical methods.

Because of the advantages of the invention discussed above, the need for extensive laboratory processing steps, with the accompanying potential for contamination of the sample, is minimized. The enriched extracts are also readily amenable to bioassay and toxicity testing techniques to define the potentially deleterious effects associated with exposure to complex mixtures of these chemicals. Also, the invention is more widely applicable to monitoring studies than any existing prior art, primarily because the invention affords much higher sampling rates (even based on the small laboratory design cited earlier), and can be used in an integrative manner for weeks due to the transformation of the polar organic chemical residues into sorbed forms in the device. The stability of polar organic chemical residues collected by any prior method is often problematic.

The invention also provides the basis for a potentially efficient remediation system applicable to effluent streams, wastewater drainage, and hazardous waste leachates. Because the polar organic chemicals are transformed into a non-mobile form and because the invention can be configured into large-scale arrangements, it is possible to deploy the devices of the invention as a treatment device for removal of a wide variety of polar organic chemicals. The sequestered polar organic chemicals are easily recovered for ultimate disposal or recycling. No other current approach for isolating such contaminants is as simple, effective and applicable to as wide a variety of aquatic systems.

Although polar organic chemicals are retained by a variety of sorbents as indicated in the references cited previously, from water percolating through the sorbent bed, no one has incorporated microporous hydrophilic polymers with water-filled pores as an uptake rate control mechanism nor has employed these agents to passively sample dissolved waterborne polar organic chemical species into sorbed, non-mobile forms in a time weighted integrative manner. In addition, no one has employed the triphasic sequestration medium of the invention to sequester a wide range of waterborne polar organic chemicals. The device of the invention is capable of being deployed for periods of weeks to months, thus providing an approach to define organism exposure in a biologically relevant manner. Unlike current methods for sampling polar organic chemicals where the usual approach involves sampling a single point in time or similar purported integrative sampling approaches that have time limits defined by mechanical operation and power requirements, research with the invention indicates that a sampling time of 28 days to be easily obtained with much greater sampling times being possible without the aforementioned mechanical or power requirement restrictions. In addition, there is no such device adequate for passive removal of polar organic chemical species from contamination sites of limited areal area. Also, there is no such device that sequesters readily bioavailable polar organic chemical residues for use in assessing exposures of humans, fish or wildlife to these potentially toxic species.

Although the invention has been described above in relation to preferred embodiments thereof, it will be readily understood by those skilled in the art that variations and modifications can be effected in these embodiments without departing from the scope and spirit of the invention.

What is claimed is:

1. A passive, integrating device for the sequestration and concentration of polar chemicals from water, said device comprising:
    a sealed microporous hydrophilic polymer membrane enclosure presenting, in use, a plurality of water-filled pores; and
    a mixed sequestration phase, contained within said membrane enclosure, for passively transforming dissolved polar organic chemicals in the water into non-mobile species in an integrative manner, said sequestration phase comprising a multiphasic admixture including a sorbent capable of sorbing and retaining polar organic chemicals.

2. A device as claimed in claim 1, wherein said sorbent comprises a carbonaceous sorbent.

3. A device as claimed in claim 2, wherein said carbonaceous sorbent is dispersed on a size exclusion styrene-divinylbenzene copolymer forming a component of said admixture.

4. Device as claimed in claim 3, wherein said admixture further comprises a polystyrene-divinylbenzene resin.

5. A device according to claim 1, wherein said membrane enclosure comprises a microporous polymer membrane.

6. A device according to claim 5, wherein said microporous membrane comprises a polymer selected from the group consisting of polyethersulfone, nylon, hydrophilic polypropylene, cellulose, and acrylic copolymers.

7. A device according to claim 6, wherein said membrane comprises a first polymer layer disposed on a second polymer layer of greater thickness than said first layer.

8. A device according to claim 1, wherein said membrane enclosure includes a microporous layer including air-filled fixed pores wherein, in use, air in the pores is exchanged with water during initial contact of the membrane layer with the water to produce said water-filled pores.

9. A device according to claim 1, wherein the membrane enclosure comprises polyethersulfone have having micropores of 0.1 $\mu$m in diameter.

10. A device according to claim 1, wherein said enclosure comprises two planar microporous members with adjacent planar surfaces thereof forming a cavity therebetween in which said sequestration phase is contained.

11. A device according to claim 10 further comprising a pair of washers secured together in side facing relation so as to retain said membranes therebetween.

12. A device for the sequestration and concentration of polar chemicals from water, said device comprising:
    a microporous hydrophilic membrane enclosure; and
    a mixed sequestration phase contained within said enclosure for transforming dissolved polar organic chemicals into non-mobile species, said sequestration phase comprising a triphasic admixture of a hyper-crosslinked polystyrene-divinylbenzene resin, and a carbonaceous sorbent dispersed on a styrene-divinylbenzene copolymer.

13. A device according to claim 12, wherein said membrane enclosure comprises a microporous polymer membrane.

14. A device according to claim 13, wherein said microporous membrane comprises a polymer selected from the group consisting of polyethersulfone, nylon, hydrophilic polypropylene, cellulose, and acrylic copolymers.

15. A device according to claim 13, wherein said membrane comprises a first polymer layer disposed on a second polymer layer of greater thickness than said first layer.

16. A device according to claim 13, wherein said microporous membrane includes air-filled fixed pores wherein, in use, air in the pores is exchanged with water during initial contact with the water.

17. A device according to claim 16, wherein the membrane comprises polyethersulfone have pores of 0.1 $\mu$m in diameter.

18. A device according to claim 12, wherein said enclosure comprises two planar microporous members with adjacent planar surfaces thereof forming a cavity therebetween in which said sequestration phase is contained.

19. A device according to claim 18 further comprising a pair of washers secured together in side facing relation so as to retain said membranes therebetween.

* * * * *